United States Patent [19]

Pontius

[11] Patent Number: 5,015,569

[45] Date of Patent: May 14, 1991

[54] ACCELERATION OF NUCLEIC ACID HYBRIDIZATION

[75] Inventor: Brian W. Pontius, Palo Alto, Calif.

[73] Assignee: Board of Trustees of Leland Stanford University, Stanford, Calif.

[21] Appl. No.: 444,179

[22] Filed: Dec. 1, 1989

[51] Int. Cl.[5] ........................ C12Q 1/68; C07H 21/00; C07K 15/18

[52] U.S. Cl. ........................................ 435/6; 435/68.1; 435/70.1; 435/820; 436/501; 536/27; 530/358; 935/9; 935/19; 935/34; 935/78

[58] Field of Search ................ 435/6, 68.1, 70.1, 820; 436/501; 536/27; 530/358; 935/9, 19, 34, 78

[56] References Cited

PUBLICATIONS

Christiansen, C. and Baldwin, R. L., "Catalysis of DNA Reassociation by the *Escherichia coli* DNA Binding Protein", *J. Mol. Biol.*, 115:441–454 (1977).

Weinstock, G. M. et al., "ATP-Dependent Renaturation of DNA Catalyzed by the recA Protein of *Escherichia coli*", *Proc. Natl. Acad. Sci. U.S.A.* (*Biochemistry*), vol. 76, No. 1, pp. 126–130 (Jan. 1979).

Cox, M. M. and Lehman, I. R., "Renaturation of DNA: a Novel Reaction of Histones", *Nucleic Acids Research*, vol. 9, No. 2, pp. 389–399 (1981).

Keener, S. L. and McEntee, K., "Homologous Pairing of Single-Stranded Circular DNAs Catalyzed by recA Protein", *Nucleic Acids Research*, vol. 12, No. 15, pp. 6127–6139 (1984).

Bryant, F. R., et al., "Kinetic Modeling of the RecA Protein Promoted Renaturation of Complementary DNA Strands", *Biochemistry*, 28:1062–1069 (1989).

Dreyfuss, G. et al., "Heterogeneous Nuclear Ribonucleoprotein Particles and the Pathway of mRNA Formation", *TIBS*, 13:86–90 (Mar. 1988).

Bandziulis, R. J. et al., "RNA-Binding Proteins as Developmental Regulators", *Genes & Development*, 3:431–437 (1989).

Williams, K. R. et al., "Amino Acid Sequence of the UP1 Calf Thymus Helix-Destabilizing Protein and its Homology to an Analogous Protein from Mouse Myeloma", *Proc. Natl. Acad. Sci. U.S.A.*, vol. 82, pp. 5666–5670, (Sep. 1985).

Cobianchi, F. et al., "Structure of Rodent Helix-Destabilizing Protein Revealed by cDNA Cloning", *The Journal of Biological Chemistry*, vol. 261, No. 8, Issue of Mar. 15, pp. 3536–3543, (1986).

Kumar, A. et al., "Purification and Domain Structure of Core hnRNP Proteins A1 and A2 and Their Relationship to Single-Stranded DNA-Binding Proteins", *The Journal of Biological Chemistry*, vol. 261, No. 24, Issue of Aug. 25, pp. 11266–11273, (1986).

Cobianchi, F. et al., "Mammalian Heterogeneous Nuclear Ribonucleoprotein Complex Protein A1", *The Journal of Biological Chemistry*, vol. 263, No. 2, Issue of Jan. 15, pp. 1063–1071 (1988).

Merrill, B. M. et al., "Phenylalanines That Are Conserved Among Several RNA-Binding Proteins Form Part of a Nucleic Acid-Binding Pocket in the A1 Heterogeneous Nuclear Ribonucleoprotein", *The Journal of Biological Chemistry*, vol. 263, No. 7, Issue of Mar. 5, pp. 3307–3313 (1988).

*Primary Examiner*—Robert A. Wax
*Assistant Examiner*—Ardin H. Marschel
*Attorney, Agent, or Firm*—Townsend and Townsend

[57] ABSTRACT

This invention relates to an improvement in nucleic acid hybridization technology. Nucleic acids bind to complementary partners in a predictable manner such that the detection of complementary partners is possible. The acceleration of the binding process is desired objective and will find broad application in a variety of industrial, medical, and research uses. In particular this invention relates to the acceleration of nucleic acid hybridization by heterogeneous nuclear ribonucleoproteins [hnRNPs].

27 Claims, No Drawings

ACCELERATION OF NUCLEIC ACID HYBRIDIZATION

The U.S. Government has a paid-up license in this invention and a right in limited circumstances to require the patent owner to license others on reasonable terms as provided for by the terms of Grant No. GM 13235, awarded by National Institutes of Health.

BACKGROUND OF THE INVENTION

1. Field of the Invention

This invention relates to an improvement in nucleic acid hybridization technology. Nucleic acids bind to complementary partners in a predictable manner such that the detection of complementary partners is possible. The acceleration of the binding process is desired objective and will find broad application in a variety of industrial, medical, and research uses. In particular this invention relates to the acceleration of nucleic acid hybridization by heterogeneous nuclear ribonucleoproteins [hnRNPs].

hnRNPs are naturally occurring proteins found in ribonuclear core particles which are approximately 20 nm in diameter and have a sedimentation coefficient of about 40S. The core particles are found in a variety of eucaryotes including fruit flies, rodents and man. The core particles are comprised of both ribonucleic acid and multiple core proteins. The precise purpose of the particles or of the role of hnRNPs are not presently understood. It is known that these particles are commonly associated with newly transcribed messenger RNA. It is presumed that they play a role in the splicing of the message.

2. Information Disclosure

The acceleration of annealing between complementary nucleic acids has been described. Christiansen C. and Baldwin, R.L., 1977, Catalysis of DNA Reassociation by the *Escherichia coli* DNA Binding Protein, J. Mol. Biol 115:441-454; Weinstock, G.M. et al., 1978, ATP-dependent renaturation of DNA catalyzed by the recA protein of *Escherichia coli*, Biochemistry 76:126-130; Cox, M.M. and Lehman, I.R., 1981, Renaturation of DNA: a novel reaction of histones, Nucleic Acid research 9:389-399; Keener S.L. and McEntree, K., 1984, Homologous pairing of single-stranded circular DNAs catalyzed by recA protein, Nucleic Acids Research 12:6127-6139; and Bryant, F.R. et al., 1989, Kinetic Modeling of the RecA Protein Promoted Renaturation of Complementary DNA Strands, Biochemistry 28:1062-1069.

Heterogeneous nuclear particles was known and reviewed by Dreyfuss, G., et al., Mar. 1988, Heterogeneous nuclear ribonucleoprotein particles and the pathway of mRNA formation, TIBS 13:86-90 and Bandziulis, R.J. et al., 1989, RNA-binding proteins as developmental regulators, Genes & Devel. 3:431-437.

The A1 core protein has been implicated in helix-destabilizing. Williams, K.R. et al., 1985, Amino acid sequence of the UPI calf thymus helix-destabilizing protein and its homology to an analogous protein from mouse myeloma, Proc. Natl. Acad. Sci. U.S.A. 82:5666-5670. The cDNA encoding A1 hnRNP from rat has been cloned and expressed. Cobianchi, F. et al., 1986, Structure of Rodent Helix-destabilizing Protein Revealed by cDNA Cloning, J of Biol. Chem. 261:3536-3543. The A1 hnRNP from human cells has been isolated and purified. Kumar, A. et al., 1986, Purification and Domain Structure of Core hnRNP Proteins A1 and A2 and Their Relationship to Single-stranded DNA-Binding Proteins, J. Biol. Chem. 261:11266-11273. Kumar et al also reported on the ability of A1 hnRNP to mediate duplex formation between synthetic polynucleotides.

The characterization of mammalian A1 hnRNP was described by Cobianchi, F. et al. 1988, Mammalian Heterogeneous Nuclear Ribonucleoprotein Complex Protein A1, J. Biol. Chem. 263:1063-1071 and by Merrill B.M. et al., 1988, Phenylalanines That Are Conserved among Several RNA-binding Proteins Form Part of A Nucleic Acid-binding Pocket in the A1 Heterogeneous Nuclear Ribonucleoprotein, J. Biol. Chem. 263:3307-3313.

SUMMARY OF THE INVENTION

The nucleic acid hybridization technology demands increasingly shorter assay times. This invention provides for a method for accelerating the rate of hybridization between two complementary nucleic acid sequences in an in vitro nucleic acid hybridization assay comprising: (a) hybridizing two complementary nucleic acid sequences in a hybridization reaction mixture under conditions permitting nucleic acid hybridization where the reaction mixture comprises heterogeneous nuclear ribonucleoprotein having a carboxy terminus capable of hnRNP/hnRNP interaction, said ribonucleoprotein present in an amount sufficient to substantially accelerate the rate of hybridization over that seen in the absence of the ribonucleoprotein; and, (b) detecting the hybridization of the two complementary nucleic acid sequences. By "capable of hnRNP/hnRNP interaction" it is meant that the carboxy termini of hnRNPs promote intermolecular hnRNP/hnRNP interactions. While bound to single stranded nucleic acid so as to facilitate complementary base pair binding. The carboxy termini of the hnRNPs of use in this invention typically exhibit little secondary structure and are rich in glycine residues. In a particular embodiment this method has the additional proviso that neither of the nucleic acid sequences being detected is a polyribouridylic acid. The preferred ribonucleoprotein is an A1 core protein such as those derived from mammalian cells. By "substantially accelerate," it is meant that a measurable increase in the rate of hybridization can be detected. Preferably, this is at least about a doubling of the hybridization rate. Accelerations of about several hundred to a thousand times have been obtained with this invention.

The above method may further embody the immobilization of one of the two nucleic acids to a solid support. Additional nucleic acids may be used to form ternary and quaternary forms of complementary strands.

The above method may further comprise the labeling of at least one of the nucleic acids with a reporter.

The above method may further comprise in step (a) an immobilized capture nucleic acid, a target nucleic acid complementary to the immobilized capture nucleic acid and a nucleic acid sequence labeled with a reporter and having a sequence complementary to a portion of the target nucleic acid different from the sequence complementary to the immobilized capture nucleic acid. This is typically designated as a sandwich assay.

The preferred amount of heterogeneous ribonucleoprotein is at least about a 5 fold excess by weight of the total amount of nucleic acid in the reaction mixture. More preferred is a 10 to 20 fold excess of protein.

The method may use DNA or RNA as nucleic acid. These may be obtained by any of a variety of techniques well known in the art.

In another embodiment, this invention provides for a method of conducting a high temperature protein-mediated nucleic acid hybridization assay having a target nucleic acid and a probe nucleic acid comprising: (a) hybridizing two complementary nucleic acid sequences in a hybridization reaction mixture under conditions permitting nucleic acid hybridization, including temperatures at about 45° C. or above, where the reaction mixture comprises a single stranded nucleic acid binding protein present in an amount sufficient to substantially accelerate the rate of hybridization above the hybridization rate in the absence of the ribonucleoprotein and where the numbers of probe nucleic acid to target nucleic acid does not approximate a 1 to 1 ratio; and (b) detecting the hybridization of the two complementary nucleic acid sequences. By "a single stranded nucleic acid binding protein" it is meant a member of the class of proteins which include RecA, A1 hnRNP and SSB. By 45° C. or above it is meant that the temperature should not exceed the temperature at which the proteins are denatured and incapable of mediating annealing. The temperature extreme will vary with the individual proteins and can be readily determined by simple and routine titration experiments. The ratio of probe nucleic acid (typically a labeled nucleic acid purposely added to the hybridization mixture) to target nucleic acid (typically the nucleic acid which is being sought or detected) is not in an equal proportions and is other than 1 to 1. Generally either of the two nucleic acids will be in excess of 10 or 100 fold of the other. Furthermore, this method may embody any of the variations described above for the previous methods.

The methods described herein may be embodied into a kit comprising compartments with nucleic acid, compartments with hybridization reagents and compartments with heterogeneous nuclear ribonucleoprotein having a carboxy terminus capable of hnRNP/hnRNP interaction. In an alternative embodiment, the kit may have the further proviso that neither of the nucleic acid sequences being detected is a polyribouridylic acid. The kits will preferably contain a A1 core protein (A1 hnRNP) such as from a mammalian cell. One of the nucleic acids in the kit may be labeled with a reporter such as an enzyme or a fluorophore.

DETAILED DESCRIPTION

A. The hnRNP

The hnRNPs of use in this invention are obtained from the core proteins of the heterogeneous nucleoprotein particle. This particle is typically made up of several different core proteins ranging from 32,000 to 42,000 daltons. The core proteins of use in this invention are distinguished by their typically being the smallest protein of the group and by their carboxy termini which are capable of hnRNP/hnRNP intermolecular attraction. The determination of hnRNP/hnRNP interactions is made through routine titration experiments where acceleration of annealing is measured (see example section). Alternatively, one can predict in some hnRNP core proteins which will accelerate hybridization by identifying the presence of a glycine-rich (approximately 40%) COOH terminus. The determination of a glycine rich termini is made by comparing the number of glycines present in the first half of the protein with the second half. (J. Biol. Chem. 263:3307-3313).

A preferred hnRNP is a human core protein typically designated A1 hnRNP. It may be obtained as a naturally occurring protein by purification from HeLa cells or as a heterologous expression product by isolation from a genetically engineered cell expressing the A1 hnRNP gene or cDNA.

The preferred method of isolating natural-occurring hnRNP is as described in detail by Kumar et al. J. Biol. Chem. 261:11266-11273, 1986. In brief this method involves the isolation of the 20-nm monoparticles from purified nuclei. The monoparticles are isolated in a sucrose density gradient. Core protein A1 is obtained by one-step chromatographic procedure which relies on the inherent tendency of the other core proteins to aggregate into polymorphic forms. The 40S particles are dialyzed into a buffer of 2.0 M NaCl to dissociate the particles. The extract is further enriched with A1 by elution through a gel filtration column in the high salt buffer with SH-reagents and collecting the appropriate fraction.

Alternatively cDNA encoding the rat A1 hnRNP has been cloned and expressed in mouse myeloma MOPC-21 cells according to Cobianchi, et al., J. Biol. Chem. 261:3536-3543, 1986. The Cobianchi reference also provides the nucleotide sequence for the rat A1 hnRNP.

The protein (about 0.5 mg/ml) is fairly stable and can be stored at −80° C. in 10 mM Tris pH 8.0, 0.1 mM EDTA, 0.1 mM dithiothreitol and 1 M NaCl. Repeated freeze thawing cycles are acceptable but not recommended.

The proteins of use in this invention function by binding to nucleic acid and by interacting in an unknown manner to facilitate hybridization of complementary nucleic acid sequences. The carboxy terminus of these proteins are required for acceleration of annealing and for intermolecular interaction (hnRNP/hnRNP interaction).

The hnRNP proteins of this invention are conserved across taxonomic genera and families. Allelic polymorphism is found within species. In addition, through recombinant genetics one, may introduce, substitute or delete various amino acids without inhibiting the ability of hnRNP to accelerate duplex formation. For example the glycine rich domain may be enriched with equivalent amino acids such as proline. This invention and the term hnRNP is meant to embrace all analogous proteins having the functional ability to accelerate annealing between nucleic acids. These proteins embrace both naturally occurring forms and synthetically modified forms.

B. Single Stranded Nucleic Acid Binding Proteins

This invention also provides for a method of accelerating hybridization at elevated temperatures (above 45° C.). The proteins of use in this method include single stranded nucleic acid binding proteins. These proteins include hnRNP and also include single stranded binding proteins and RecA. Such proteins are known in the art as mediators of nucleic acid annealing. (See for example J. Mol. Biol. 115:441; Proc. Natl. Acad. Sci. U.S.A. 82:5666-5670; and Biochemistry 28:1062-1069).

The reaction conditions are as provided below for hnRNP, although optimal reaction conditions may require some routine titration experiments (e.g., the addition of magnesium).

C. Accelerating the rate of hybridization for nucleic acid hybridization assays Nucleic acid hybridization assays are well known in the art. This invention is not limited to any particular mode of practicing these assays. Hybridization techniques are generally described in Nucleic Acid Hybridization a Practical Approach, Ed. Hames, B.D. and Higgins, S.J., IRL Press 1987. As improvements are made in hybridization techniques, they can readily be applied to this invention.

The acceleration of nucleic acid annealing has many uses. The uses include Northern and Southern analyses, subtractive hybridization, plaque colony screening using nucleic acid probes, and the polymerase chain reaction amplification process. Clinical applications include: diagnostic assays for pathogens, and disease states; and genetic profiling for medical or forensic uses.

1. Hybridization Conditions

Various hybridization solutions may be employed in the reaction mixture. Standard hybridization solutions often contain protein denaturants such as detergents, polar organic solvents such as formamide or guanidine salts. Such solutions are not recommended for protein mediated assays. The preferred solutions for this invention have a pH of between about 4.0 and about 10, most preferably between pH 6 and 8. EDTA may be included in the hybridization solutions.

Standard salt conditions for hybridization assays include the use of monovalent salts (e.g., potassium or sodium) in concentrations of 1 mole or greater. Under the conditions such as provided in the examples below, high concentrations of monovalent cations have been noted as inhibiting hnRNP mediated acceleration of annealing. Although hybridization conditions may possibly be varied to obtain acceleration of annealing under high salt conditions, it is recommended that the total monovalent salt concentration be kept between about 80 and 120 mM.

Minor amounts of magnesium salts, non-specific blocking agents such as bovine serum albumin may be included in the hybridization reaction mixture. In addition, the hybridization solutions may optionally contain unlabeled carrier nucleic acids from about 0.1 to 5 mg/ml fragmented nucleic acid, DNA, e.g., fragmented calf thymus DNA or salmon sperm DNA, or yeast tRNA or yeast RNA. Other additives may also be included, such as the volume exclusion agents (e.g., dextran sulfate at about 5–10% w/v).

The recommended quantity of hnRNP is dependent upon the quantity of nucleic acid present in the reaction mixture. The hnRNP is thought to coat the nucleic acid with multiple hnRNP bound to each strand. For effective acceleration of annealing, a minimum of a five fold excess of hnRNP by weight over the total weight of nucleic acid present in the reaction mixture is recommended. More preferred is a 10–20 fold excess of protein by weight over the total nucleic acid. Where nucleic acid concentrations are very low, increased amounts of hnRNP may be required.

Reaction temperatures will influence the hybridization rates even in the presence of hnRNP. The reaction temperature conditions are between 20°–80° C. or above, and preferred temperatures are 37°–65° C. There is a noticeable increase in acceleration of annealing as temperatures increase with 65° C. being a preferred reaction temperature for hybridization.

By "nucleic acid sequences", it is meant that the nucleic acids are in a polymeric form. Typically these are the naturally occurring 5'–3' covalent bonds forming a phosphodiester backbone. Both natural and synthetic polymers are operable in this invention. Such synthetic polymers would include unnatural bases and variations in the natural 5' to 3' bonding. The size of the sequence is not critical. Typically the polymers are of a size to permit hybridization to be sufficiently specific to function successfully in the assay and avoid nonspecific binding to non-targets. Preferably the polymers are about 33 nucleotides long—— up to several kilobases. Exact complementarity between strands is not required. By varying the stringency of the hybridization mixture, one can achieve satisfactory results with strands of nucleic acid that are not exact complements of each other.

2. Modes of Hybridization Assays

Nucleic acids hybridizations may be run in a variety of modes. It is expected that one of skill is familiar with nucleic acid hybridization assays and no attempt is made here to describe in detail the various modes available to workers in the field. The acceleration of annealing with hnRNP can be achieved in both homogeneous and heterogeneous nucleic acid hybridization assays.

Homogeneous nucleic acid hybridization assays involve assays where both complementary nucleic acids are free in solution. Heterogeneous assays involve the immobilization of at least one nucleic acid polymer to a solid support. These supports include but are not limited to filter papers, gels, nylon, magnetic beads, glass, carboxy and amino activated inert solids such as teflon or plastics. Immobilization can be non-covalent through ionic or hydrogen bonding interactions or through covalent bonding. Heterogeneous assays are well known in the art.

The reaction modes include but are not limited to binary, ternary or quaternary levels. Binary modes are reactions which rely only upon annealing between two separate nucleic acids, one of which is typically labeled. Ternary and quaternary modes involve sandwich assays where multiple nucleic acid polymers are annealing to each other.

3. Detection of Hybridization

The hnRNP mediated annealing does not effect the means for detection of hybridization. All standard methods are useful. These include radioisotopes, fluorophores (e.g., fluorescein) and enzymes (e.g., horseradish peroxidase or alkaline phosphatase) as reporters or labels. The reporters can be either directly attached to one of the nucleic acid polymers or indirectly attached through a ligand/receptor configuration. Methods for detection are well known in the art and variations and improvements are within the scope of this invention.

All references are incorporated by reference herein. The following examples are offered by way of illustration and not by way of limitation.

EXAMPLES

1. The acceleration of nucleic acid hybridization using A1 hnRNP

A comparison of nucleic acid hybridization rate in the presence of A1 hnRNP and in its absence demonstrates the dramatic hnRNP mediated increase in the rate of hybridization. The assays used nucleic acid from a Hind III/Bgl II digestion of plasmid pSV2gpt (Science 209:1422–1427, 1980). The double stranded segment used has 120 nucleic acid bases per strand and comprises a DNA segment adjacent to the xanthine guanine phosphoribosyl-transferase gene from *E coli*. Both strands were end labeled with $^{32}P$ by filling the recessed 3' ends according to Maniatis, T., Fritsch, E.F., and Sambrook, J., 1982, Molecular Cloning: A Laboratory Manual, Cold Spring Harbor Laboratory, Cold Spring Harbor, N.Y. [Maniatis] (at page 113). The count was approximately $10^8$ cpm per microgram of nucleic acid.

The nucleic acid was placed in a hybridization reaction mixture of 20 μl containing, 10 mM potassium phosphate pH 7.0, 1 mM EDTA, 100 mM NaCl, 1.25 ng/ml of the end-labeled complementary nucleic acid (previously rendered single stranded by heating at 95° C. for 5 minutes with 10 mM potassium phosphate buffer/1 mM EDTA and rapid chilling in ice water until added to the reaction mixture), and 711 ng/ml of A1 hnRNP (added last to the experimental mixtures). The reaction mixtures were incubated at 65° C. for 0, 1, 2, 4, 8, 16 and 32 minutes.

The reactions were stopped by diluting 5 μl of the reaction mixture to 20 μl final volume of solution containing 0.1% SDS, 50 μg/ml tRNA, 5% glycerol, and 0.05% bromphenol blue. The reaction products were then extracted with phenol:chloroform (1:1) and the aqueous phase was loaded onto a 10% polyacrylamide gel and electrophoresed for 2 hours at 10 V/cm. The gels were run in a Tris/borate buffer according to Maniatis (1982 at page 454) The gels were then dried and subjected to autoradiography to determine the extent of hybridization. The extent of hybridization was readily determined by comparing the density of single stranded DNA to double stranded DNA in each lane on the gels. Under the given conditions, there is no appreciable annealing detected after 32 minutes without A1 hnRNP. The half-time for annealing under the identical conditions with A1 hnRNP present is less than about 1 minute.

2. The influence of A1 hnRNP on acceleration of nucleic acid hybridization rates compared to standard hybridization conditions The reaction conditions were identical to those given in example 1 except reaction mixture A contained 120 mM potassium chloride and 400 ng/ml A1 hnRNP. Reaction mixture B contained 1 M NaCl representing standard hybridization conditions. Reaction mixture A was incubated for 5 minutes at 65° C. and mixture B was run for 5 minutes at 68° C. The autoradiographic results indicated that after five minutes, reaction mixture A contained 100% duplexed nucleic acid and no detectable single stranded nucleic acid. Mixture B had no detectable double stranded nucleic acid. The relative acceleration was estimated to be at least 100 fold faster due to A1 hnRNP.

3. The influence of temperature upon the A1 hnRNP mediated acceleration of nucleic acid hybridization rates The reaction conditions were identical to the reaction conditions provided in example 1 except the mixtures had 4000 ng/ml A1 hnRNP. The reaction mixtures were incubated for 5 minutes at 0° C., 23° C., 37° C., 50° C. and 65° C. The results demonstrated that acceleration was optimized at the higher temperatures with 100 percent of the label being associated with the double stranded nucleic acid at 65° C. after 5 minutes and about 50% of the label being found in the double stranded nucleic acid after 5 minutes at 37° C.

4. A1 hnRNP mediated acceleration of nucleic acid hybridization in the presence of excess heterologous DNA To establish that A1 hnRNP would accelerate nucleic acid hybridization in the presence excess heterologous DNA such as would be found in a clinical sample, reactions were run in the presence of M13MP18 single stranded DNA (M13−) or M13MP18 single stranded DNA having the same 120 bp target sequences, as described above, cloned into it (M13+). The reaction conditions were identical to example 1 except the A1 hnRNP was at 16,000 ng/ml. The temperature was at 65° C. and each reaction was allowed to hybridize for 5 minutes. Reaction mixture A contained no heterologous DNA. Reaction mixture B contained a 1000 fold excess of only M13− (25ng). Reaction mixture C contained M13− (22.5 ng) and M13+ (2.5 ng). Reaction mixture D contained only M13+ (25 ng). After 5 minutes at 65° C., the hybridizations were completed. No significant inhibition of hybridization was detected in mixture B over mixture A. No significant inhibition of hybridization was noted in mixtures C and D wherein it was clearly established that the placement of the target within flanking noncomplementary sequences does not significantly inhibit the ability of A1 hnRNP to effectively accelerate the hybridization rates. Similar results were obtained with boiled genomic DNA replacing the M13MP18 DNA. No strong preference was noted for the annealing of the short nucleic acids (probes) to the target sequences regardless of whether the target was a short fragment or a part of a larger fragment (cloned into a M13 DNA). Moreover, the experimental results were analogous when the hybridizations were run at 37° C. although hybridization rates are slower.

Although the foregoing invention has been described in some detail by way of illustration and example for purposes of clarity of understanding, it is obvious that certain changes and modifications may be practiced within the scope of the appended claims.

What is claimed is:

1. A method for accelerating the rate of hybridization between two complementary nucleic acid sequences in an in vitro nucleic acid hybridization assay comprising:
   (a) hybridizing two complementary nucleic acid sequences in a hybridization reaction mixture under conditions permitting nucleic acid hybridization where the reaction mixture comprises heterogeneous nuclear ribonucleoprotein having a carboxy terminus capable of hnRNP/hnRNP interaction, said ribonucleoprotein present in an amount sufficient to substantially accelerate the rate of hybridization above the hybridization rate in the absence of the ribonucleoprotein; and
   (b) detecting the hybridization of the two complementary nucleic acid sequences with the proviso that neither of the nucleic acid sequences being detected is a polyribouridylic acid.

2. A method of claim 1 wherein the ribonucleoprotein is an A1 core protein.

3. A method of claim 1 wherein the ribonucleoprotein is a mammalian A1 core protein.

4. A method of claim 1 wherein the carboxy terminus of the ribonucleoprotein is glycine rich.

5. A method of claim 1 wherein the A1 core protein is derived from a rat.

6. The method of claim 1 wherein the method further comprises the immobilization of one of the two nucleic acids to a solid support.

7. The method of claim 1 wherein the method further comprises the labeling of one of the two nucleic acids with a reporter.

8. A method of claim 1 wherein the method further comprises in step (a) an immobilized nucleic acid, a target nucleic acid complementary to the immobilized nucleic acid and a nucleic acid sequence labeled with a reporter and having a sequence complementary to a portion of the target nucleic acid different from the sequence complementary to the immobilized capture nucleic acid.

9. A method of claim 1 wherein the amount of heterogeneous ribonucleoprotein is at least about a 5 fold excess by weight of the total amount of nucleic acid in the reaction mixture.

10. A method of claim 1 wherein the amount of heterogeneous ribonucleoprotein is at least about a 10 fold excess by weight of the total amount of nucleic acid in the reaction mixture.

11. A method of claim 1 wherein the amount of heterogeneous ribonucleoprotein is at least about a 20 fold excess by weight of the total amount of nucleic acid in the reaction mixture.

12. A method of claim 1 wherein the nucleic acid sequences are polynucleotides of at least 33 nucleotides.

13. A method of claim 1 wherein the nucleic acid is a polynucleotide of DNA.

14. A method of claim 1 wherein the nucleic acid is a polynucleotide of RNA.

15. A method for accelerating the rate of hybridization between two complementary nucleic acid sequences in an in vitro nucleic acid hybridization assay comprising:
    (a) hybridizing two complementary nucleic acid sequences in a hybridization reaction mixture under conditions permitting nucleic acid hybridization where the reaction mixture comprises heterogeneous nuclear ribonucleoprotein having a carboxy terminus capable of hnRNP/hnRNP interaction, said ribonucleoprotein present in an amount sufficient to substantially accelerate the rate of hybridization above the hybridization rate in the absence of the ribonucleoprotein; and
    (b) detecting the hybridization of the two complementary nucleic acid sequences.

16. A method of claim 15 wherein the nucleic acid sequences are a polynucleotides of at least 33 nucleotides in length.

17. A method of claim 15 wherein the nucleic acid is a polynucleotide of DNA.

18. A method of claim 15 wherein the nucleic acid is a polynucleotide of RNA.

19. A method of claim 15 wherein the amount of heterogeneous ribonucleoprotein is at least about a 5 fold excess by weight of the total amount of nucleic acid present in the reaction mixture.

20. A method for conducting a high temperature protein-mediated nucleic acid hybridization assay having a target nucleic acid and a probe nucleic acid comprising:
    (a) hybridizing two complementary nucleic acid sequences in a hybridization reaction mixture under conditions permitting nucleic acid hybridization, including temperatures at about 45° C. or above, where the reaction mixture comprises a single stranded nucleic acid binding protein present in an amount sufficient to substantially accelerate the rate of hybridization above the hybridization rate in the absence of the ribonucleoprotein and where the numbers of probe nucleic acid to target nucleic acid does not approximate a 1 to 1 ratio; and
    (b) detecting the hybridization of the two complementary nucleic acid sequences.

21. A method of claim 20 where the single stranded nucleic acid binding protein is a heterogeneous nuclear ribonucleoprotein having a carboxy terminus capable of hnRNP/hnRNP interaction.

22. A method of claim 20 where the temperature is about 65° C.

23. A method of claim 22 where the nucleic acid sequences are DNA.

24. A kit for the detection of nucleic acid hybridization comprising a compartment with nucleic acid, a compartment with hybridization reagents, and a compartment with heterogeneous nuclear ribonucleoprotein having a glycine-rich carboxy terminus said ribonucleoprotein with the proviso that neither of the nucleic acid sequences being detected is a polyribouridylic acid.

25. A kit of claim 24 wherein the ribonucleoprotein is an A1 core protein.

26. A kit of claim 24 further comprising a compartment having a nucleic acid labelled with a reporter.

27. A kit of claim 26 wherein the reporter is selected from the group consisting of an enzyme and fluorophore.

* * * * *